United States Patent [19]

Torgeson

[11] Patent Number: 4,706,292

[45] Date of Patent: Nov. 10, 1987

[54] SPEECH PROSTHESIS

[75] Inventor: W. Lee Torgeson, Pittsburgh, Pa.

[73] Assignee: Joseph A. Resnick, Natrona Heights, Pa.

[21] Appl. No.: 785,259

[22] Filed: Oct. 7, 1985

[51] Int. Cl.⁴ ............................................... A61F 1/20
[52] U.S. Cl. ....................................... 381/70; 623/9
[58] Field of Search ........................... 381/70; 3/1.3

[56] References Cited

U.S. PATENT DOCUMENTS

| 4,502,151 | 2/1985 | Castle | 381/70 |
| 4,539,699 | 9/1985 | Katz et al. | 381/70 |
| 4,547,894 | 10/1985 | Benson | 381/70 |
| 4,550,427 | 10/1985 | Katz et al. | 381/70 |
| 4,571,739 | 2/1986 | Resnick | 381/70 |

OTHER PUBLICATIONS

Schoendorfer, D. W., "The Development of an Internally Worn Vocal Prosthesis", *Journal of Clinical Eng.*, Jan.–Mar. 1979, vol. 4, No. 1, pp. 29–38.

*Primary Examiner*—Gene Z. Rubinson
*Assistant Examiner*—L. C. Schroeder

[57] ABSTRACT

In a speech prosthesis, a direct radiator speaker, a rubber membrane over a speaker for sealing against liquid and food, and an O-ring seal for a battery compartment.

10 Claims, 15 Drawing Figures

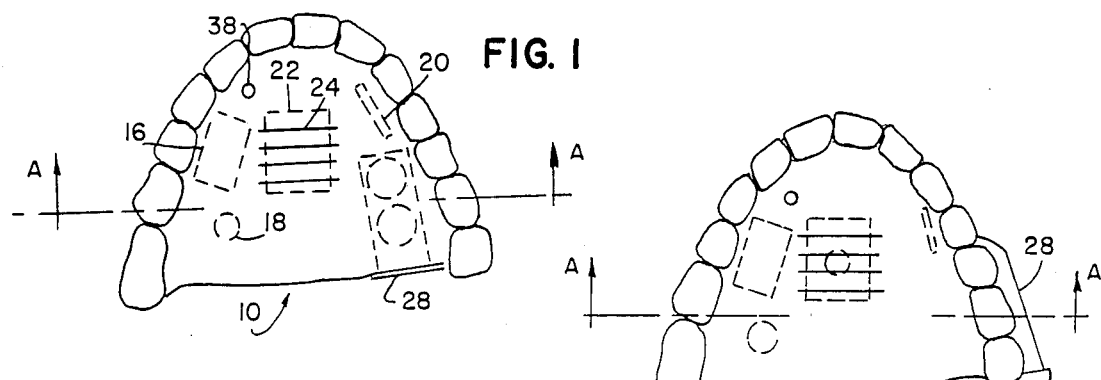
FIG. 1
FIG. 2
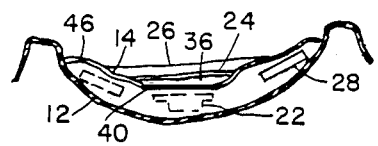
FIG. 1A
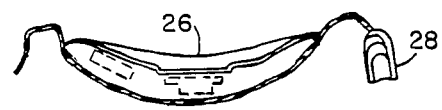
FIG. 2A
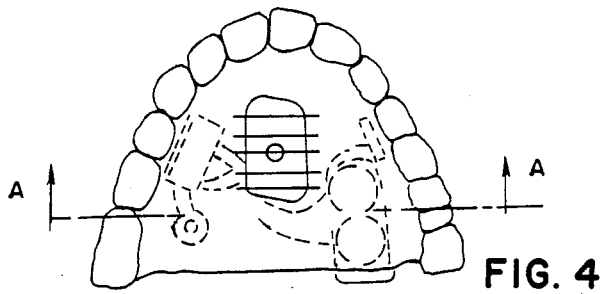
FIG. 4
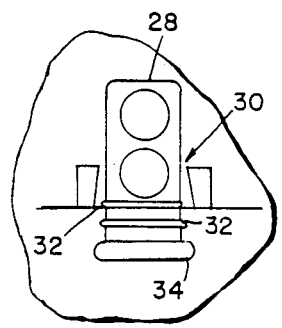
FIG. 4B
FIG. 4A

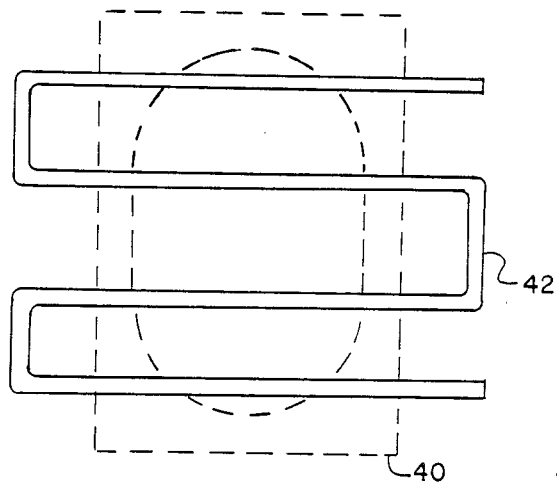
FIG. 3A
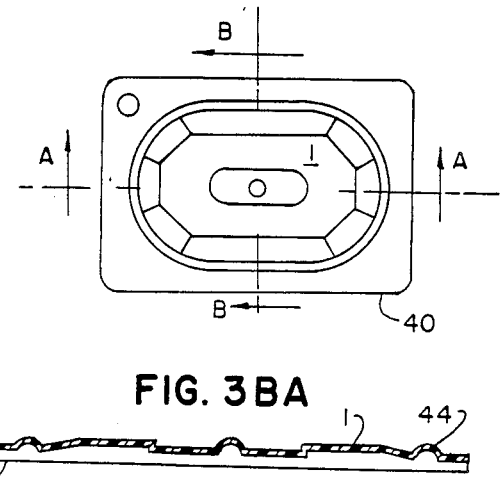
FIG. 3B
FIG. 3BA
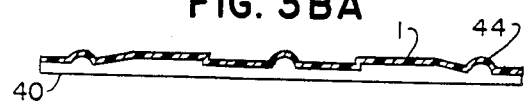
FIG. 3BB
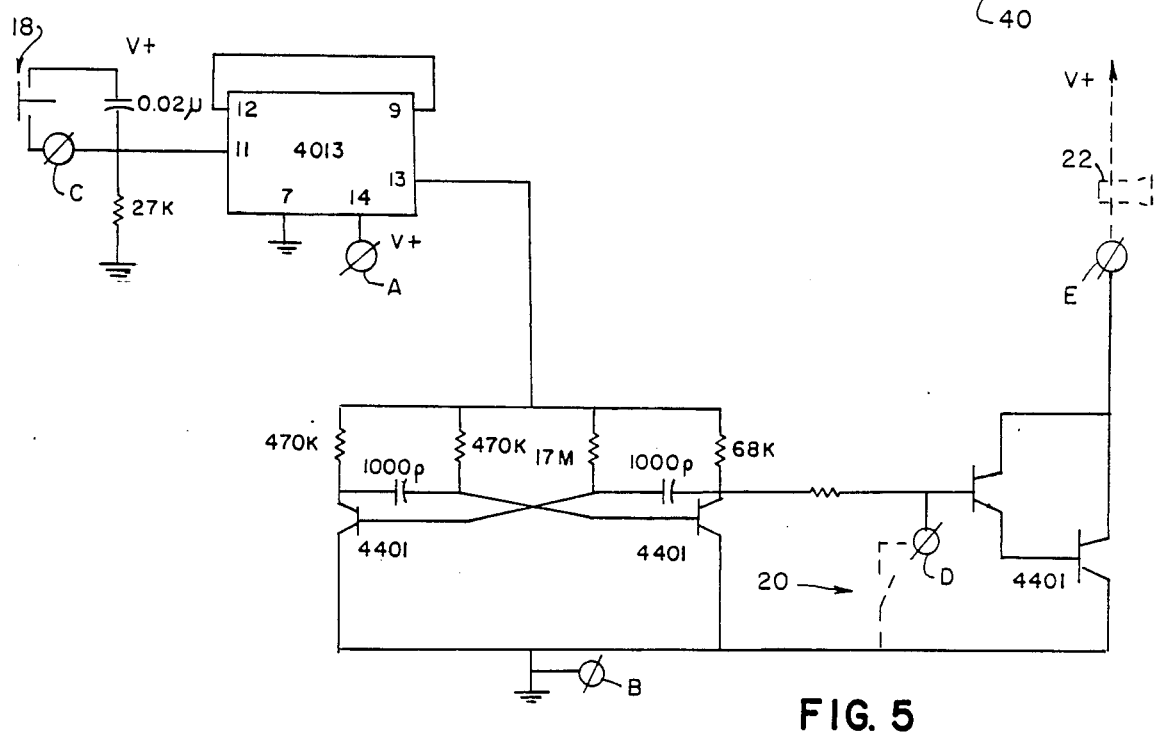
FIG. 5

SPEECH PROSTHESIS

FIELD OF THE INVENTION

The present invention relates to a device for overcoming the loss of speech or for supplementing speech, as in the case of speech deficiencies.

SUMMARY

It is an object of the invention to provide an improved speech prosthesis with improved acoustic output, including improved output in the frequency range from about 250–1000 Hz.

This as well as other objects which will become apparent in the discussion that follows, are achieved according to the present invention by providing in a speech prosthesis a direct radiator speaker, a rubber membrane over a speaker, and an O-ring seal for a battery compartment.

BRIEF DESCRIPTION OF THE DRAWING

FIG. 1 and 1A include in its upper half a view upwards towards the hard palate of a patient, showing teeth of the upper jaw and an embodiment of the speech prosthesis in place, and in its lower half a section thereof taken along the cutting plane A—A of the upper half.

FIG. 2 and 2A are similar to FIG. 1 and show a different embodiment of the battery emplacement.

FIG. 3A is a detail view of a speaker protection as in FIG. 1.

FIG. 3B, 3BA and 3BB are detail views of a speaker modification for use as in FIG. 1.

FIG. 4, 4A, and 4B are similar to FIG. 1 and includes a detail views of the battery emplacement.

FIG. 5 shows an electrical system for use with the prosthesis.

DESCRIPTION OF THE PREFERRED EMBODIMENTS

Figure 6:
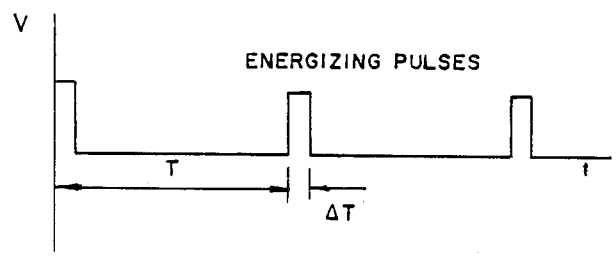
FIG. 6 shows energizing pulses for pulsing the speaker.

The speech prosthesis is formed of fabricated parts and materials which are assembled with dental prosthetic elements to form the prosthesis.

One version of the prosthesis accomodates all components of the device in a palatal plate. An alternative version, used for persons with missing upper molars and a premolar on one side of the jaw, places the battery carrier in the false teeth.

FIG. 1 shows the approximate locations of the various components of the prosthesis in a first version. These components are installed in or on a plate 10, which is fabricated from dental acrylic. The plate has two parts: a thin lower palatal element 12 which is molded from a cast of the patient's palate and an upper palatal emement 14 which defines the outer surface of the prosthesis. The terms "upper" and "lower" are on the basis of the orientation of Section A—A. In actual installation in the mouth of a patient, the lower palatal element 12 would be in contact with the patient's palate, and the upper palatal element 14 would be below. The upper element 14 would be the element closer to the patient's tongue. Together, the lower and upper elements enclose a volume of about 5 cm$^3$, which serves as a resonating space and to house other components of the prosthesis. The plate formed of elements 12 and 14 is like an upper plate for carrying false teeth. It is thickest at its center and is thinned at its edges and particularly toward the patient's throat, to guard against the gag reflex.

The electronics package 16, termed the "hybrid", the master on/off switch 18, reed switch 20, speaker 22, with its protective grille, or grid, 24, the silicone rubber membrane 26, and battery carrier 28 are installed directly on the upper palatal element 14. The upper element is then assembled with the lower element 12 such that the two elements have a line of mutual contact along their outer edges, and 3M 4693 adhesive is supplied at the contact to seal and enclose the internal volume containing the hybrid, the speaker, and the batteries. The membrane 26 is cut generally to the outline of the upper palatal element and sealed to this element 14 using some primer to soften the acrylic material of the element surface and RTV (room temperature vulcanizing, water curing, such as Type A Dow-Corning RTV) cement only along the outside edge of the element, near the line of mutual contact with the lower element. There being a gap and no attachment of the membrane to element 14 inwardly of the edge of the element, the membrane is left free to expand under any pressure differences between the inside of the prosthesis and its environment and to vibrate in response to sound emitted from speaker 22.

Speaker 22 is a direct radiator in that it does not have any horn attached to it. Its orientation when the prosthesis is installed in a patient's mouth is downwards toward the tongue, the plane of its sound radiating diaphragm thus being generally parallel to the tongue.

Prostheses fabricated for clinical testing have also accomodated the batteries in false teeth attached to the upper palatal element as shown in FIG. 2. See, in this connection U.S. patent application Ser. Nos. 319,039 and 533,002 filed, respectively, Nov. 6, 1981, and Sept. 16, 1983, by Joseph A. Resnick.

FIG. 3A shows the detail of an embodiment of grid 24 and its location over the frame 40 of the speaker 22. The grid is formed from 0.030 stainless steel wire. It is attached at its extremities, such as extremity 42, on either side of the speaker frame to the upper palatal element with dental acrylic/monomer. A recess can be provided in the upper element 14 around the edge of the speaker for this purpose, using appropriate molding fixtures to define the shape of the PMMA during curing. There is a small space between the grid 24 and the speaker 22 and its frame 40, as shown in Section A—A in FIG. 1, such that deflection of grid 24 by accidental contact will not bring grid 24 into contact with the speaker.

FIG. 3B shows details of the speaker construction around frame 40. As supplied from the manufacturer, the speaker exposes within frame 40 an aluminum foil of about ½-mil thickness. As shown in this figure, this aluminum foil is protected by a 4-mil Mylar cover 1. Shrink-wrapped around the outside of the cover 1 is a 2-mil Surlyn rim. The assembly is bonded together by 3M 4693 elastomer adhesive. Flex beads 44 are provided in these sheet materials so as to provide for proper vibration of the sheet materials at audio frequencies.

FIG. 4 adds an indication of the electrical wiring of the various components together, and additionally provides a detail of the battery installation.

The same battery carrier 28 can be used with either version. It is made of a strip of silicone rubber and is flexible to adapt to the shape of the cavity provided to house it, for instance the cavity between the palatal elements in FIGS. 1 and 4. The holes receiving the button batteries are slightly smaller than the diameter of the batteries, so as to distend upon insertion of the batteries to hold the batteries securely in place. A tapered opening 30 for the battery carrier is formed by pressure molding acrylic around a tapered mandrel to produce a smooth, tapered passageway. Positive sealing of the battery opening is obtained by means of two O-rings 32 which are attached and sealed to grooves in the battery carrier with Type A Dow-Corning RTV. When the protruding end 34 of the battery carrier as shown in the detail of FIG. 4 is pushed on, the O-rings seat firmly against the opening 30 to prevent leakage of saliva and liquids into the battery container. Two O-rings are used to reduce the possibility that sealing will be compromised by foreign matter lodged in the opening. The battery contacts can be molded directly into the acrylic.

Prototype prostheses have been essentially "handmade". However, the assembly of production devices can easily make use of fixtures for forming sheets of uncatalyzed dental PMMA to fabricate the plastic parts of the prosthesis. For example, it is anticipated that the opening 36 for the speaker, and the battery cavity, would both be shaped by using fixtures (probably rubber) designed to conform to the contours of the patient's palate and teeth (or dentures).

If the prosthesis is entirely contained in a palatal plate, it is necessary to place the battery opening in the lower element 12 of the plate. In this case, the upper element will be shaped to fit around the battery opening so that a sealed palatal space is obtained. A sufficient length of flexible twoconductor wire will be used in this case to connect the batteries to the hybrid electronics package prior to assembly.

It will be noted from FIGS. 1 and 2 that the speaker is thus protected from forces due to handling as well as temperature and pressure changes by means of (1) a silicone rubber membrane 26 attached to the periphery of the palatal surface, (2) a protective grid over the face of the speaker, and (3) the Mylar and Surlyn sheet materials.

Hole 38 in the upper palatal element, located under the membrane, prevents the development of a static pressure difference across the speaker. Elimination of pressure across the speaker is important, particularly in the case of an armature speaker, such as the Knowles speaker specified below, because the pressure difference can act on the diaphragm to force the armature into contact with a pole piece, such that the speaker is rendered inoperable. Appreciable pressure differences can be caused by changes in elevation, such as can occur in an elevator, and by temperature changes. Bringing the prosthesis from a room temperature of 70 deg. F. to 98 deg. F. body temperature leads to a 6% gas volume change, such that there is a net gas flow through hole 38 into the space between silicone rubber membrane 26 and upper palatal element 14. This extra gas volume is accomodated without discomfort to the patient by stretching of the membrane 26. Alternatively, a plugged hole (not shown) into the upper palatal element 14 can be provided at location 46 in Section A—A of FIG. 1, so that the user of the prosthesis can release excess stretching of membrane 26 such as might occur in an airplane.

Use of the thin silicone rubber membrane 26 sealed to the periphery of the palatal prosthesis and covering both the loudspeaker 22 and the master on/off switch 18 is quite advantageous. The membrane serves several functions: protection of the speaker from mechanical damage, since only pressure forces can be transmitted to the speaker (suction forces merely inflate the membrane); sealing of the face of the prosthesis including the speaker and switch 18 against the intrusion of liquids; increase in the vibrating area of the sound radiator, with improved low frequency output. It is preferred with respect to the effect of the membrane on the sound output of the prosthesis that the minimum distance across membrane 26 as measured in the plane of the upper part of FIG. 1 be greater than the speaker diaphragm as measured in the same plane; more preferably, this minimum distance across the membrane is at least twice the minimum distance across the speaker diaphragm.

Voice-coil speakers, due to their different construction from armature speakers, are less sensitive to pressure differences.

The plate comprised of the lower and upper elements 12 and 14 is held in place in a patient's mouth using techniques used in the dental field for holding the plate of a denture in place.

Figure 7:
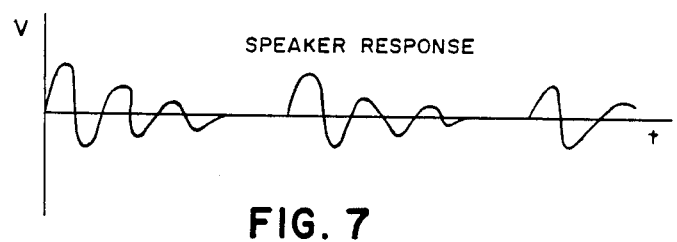
FIG. 7 shows the speaker response.

FIG. 5 shows the electrical system of the prosthesis. During speaker operation, the speaker is pulsed periodically, by pulses as shown in FIG. 6. Between pulses, the speaker oscillates with decreasing amplitude, as illustrated in FIG. 7.

The main circuit includes four transistors (4401's) and the associated resistors and capacitors. The two transistors on the left of FIG. 5 with their associated resistors and capacitors comprise a conventional non-symmetrical square-wave oscillator. The output voltage at the junction of the 1000 pF capacitor and the 68 K resistor has the waveform shown in FIG. 6. The period T is determined by the 17 M resistor and adjoining 1000 pF capacitor. The pulse duration, delta T, is determined by the 470 K resistor (next to the 17 M resistor) and the adjoining 1000 pF capacitor.

The output of the flip-flop is coupled through a 430 K resistor to a Darlington configuration of two transistors. When a pulse is applied to this Darlington configuration, the transistors saturate and act as a closed switch, thus connecting one end of the coil of the speaker to ground, while the other end is connected to V+, energizing the speaker.

When the base of the Darlington input transistor is shorted to ground via the magnetic reed switch 20, the Darlington "switch" remains open regardless of the output of the oscillator and no sound is produced by the speaker. The magnetic reed switch is closed under the action of a magnet associated with a tooth on the lower jaw of the patient, when the mouth is closed. When the mouth is opened, the increased separation of the magnet from the reed switch allows the switch to open. This is as explained in U.S. Pat. Application Ser. Nos. 319,039 and 533,002 filed, respectively, Nov. 6, 1981, and Sept. 16, 1983, by Joseph A. Resnick.

To turn the oscillator on, V+ must be applied to the junction of the two 470 K, the 17 M and the 68 K resistors. This is achieved by applying the output of a 4013 T-flip-flop ("toggle switch") to the junction.

The application and removal of V+ directly would require an on-off switch (single-pole-single-throw, SPST). Such a switch is large and difficult to operate with the tongue. Instead, the system uses a push-button toggle switch. The toggle action is obtained with the T-flip-flop 4013. The associated capacitor and resistor acts as a debouncer to mask the bouncing or chatter of the mechanical push button 18 when the patient depresses it with the tongue.

Figure 8:
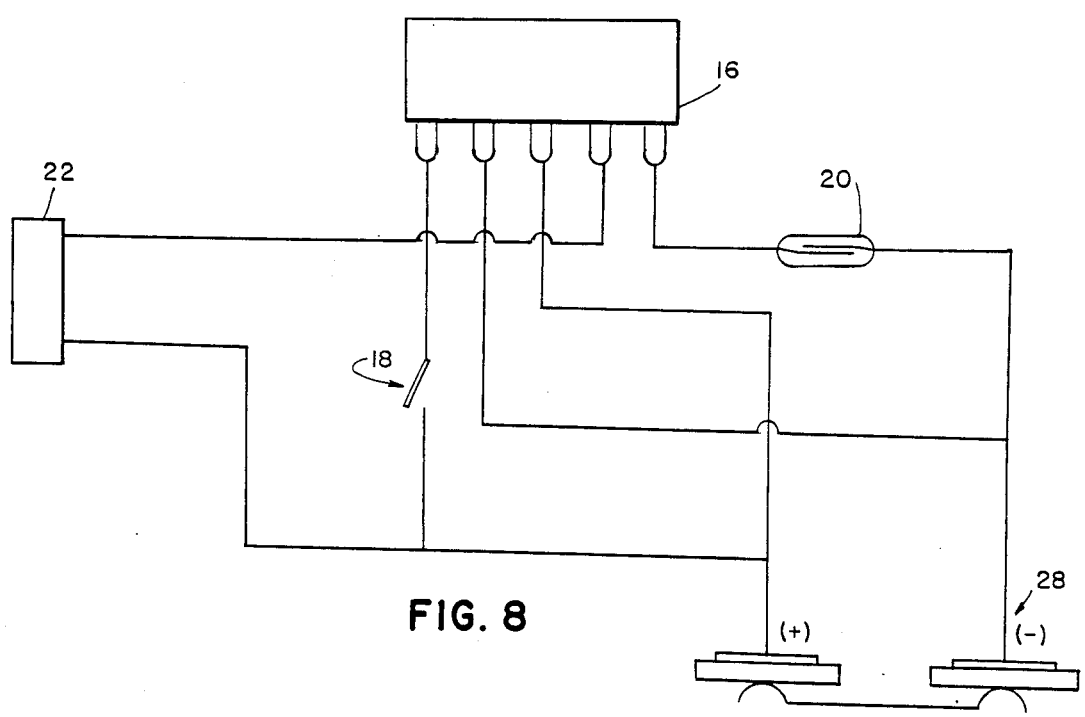
FIG. 8 is a schematic representation of the electrical system.

FIG. 8 provides a schematic view of the electrical system.

Component parts of the prosthesis are as follows:

1. Magnet for operating reed switch - sintered Alnico 2, Part No. 28C86A, of Permag Magnetics Corp., Toledo, Ohio.

2. Batteries - lithium/manganese dioxide; 3 v. Sanyo CR 1220, Sanyo Electric, Inc., Little Ferry, N.J..

3. Reed switch - Hermetic switch HSR 003 DT-C (pull up range 5-10). Hermetic Switch, Inc., Chickasha, OK.

4. Loudspeaker - Modified Knowles TB-4. In addition to the modifications discussed above, the armature is permanenetly bent to reduce the magnetic gap from 0.007/0.007 (symmetrical) to 0.002/0.012., these being the spacings from the tip of the armature to the pole pieces. The armature can be bent in this manner by using tools to bring force to bear on the base of the amrature which is accessible through a narrow gap between the coil and the lower pole piece. These adjustments can be carried out without disassembly of the speaker and tested in an appropriate fixture to ensure correct operation of the speaker. In a production embodiment, the speaker would, of course, be supplied with the modifications already carried out; adjustment of the armature could also be done by the supplier or on final assembly of the prostheses. The TB-4 is available from Knowles Electronics Inc., Franklin Park, Ill.

5. Battery carrier - Made as shown in the drawings, molded from MDX Type 4515 silicone rubber of Dow-Corning.

6. O-rings - PAI size 40-370, silicone rubber from Precision Associates, Inc., Minneapolis, Minn..

7. Membrane 26 - molded from MDX Type 4515 silicone rubber (Dow-Corning). 3-5 mil thickness.

8. Hybrid electronics module - Hydelco, Inc., Newbury Park, CA.

9. Surlyn Type 8020 - E.I. duPont de Nemours & Co., Inc..

The loudspeaker emplacement as above described has a resonant frequency in the range from 300-600 Hz, an important feature for a speech prosthesis. The reason for this is that the lowest formants lie in this range; also, it should be noted that the frequency range for telephone transmission is approximately 300-3000 Hz. This response additionally provides very satisfactory speech quality.

Factors which control the resonant frequency are:
1. The mechanical stiffness of the speaker suspension;
2. The mechanical stiffness of the air space inside the prosthesis; and
3. The speaker mass and damping.

The membrane 26 placed over the upper palatal element 14 increases the vibrating mass and acoustic loading of the speaker and affects, to a lesser degree, the stiffness of the vibrating system.

The further modifications of the Mylar and Surlyn sheets on the diaphragm and the offset adjustment of the speaker armature contribute to lowering the resonant frequency and increasing sound output.

What is claimed is:

1. A speech prosthesis comprising a plate, a hornless, direct radiator speaker carried by the plate, and a membrane means sealed around the plate for protecting the speaker from liquids and food and free centrally to vibrate in response to sound from the speaker, the membrane means increasing the vibrating area of the speaker, for improving low frequency output.

2. A prosthesis as claimed in claim 1, the plate comprising upper and lower palatal elements enclosing the speaker.

3. A prosthesis as claimed in claim 2, the plate having means for enabling gas flow from within the plate into contact with the membrane means.

4. A prosthesis as claimed in claim 3, the plate containing an electrical means for driving the speaker.

5. A prosthesis as claimed in claim 4, further comprising an on/off switch means on the plate and protected by the membrane, the switch means permitting tongue actuation for enabling and disabling the electrical system.

6. A prosthesis as claimed in claim 1, the speaker being an armature speaker.

7. A prosthesis as claimed in claim 1, the speaker being a voice-coil speaker.

8. A speech prosthesis comprising a hornless, direct radiator speaker and a membrane means for protecting the speaker from liquids and food, the membrane means being free to vibrate in response to sound from the speaker, the membrane means increasing the vibrating area of the speaker, for improving low frequency output.

9. A prosthesis as claimed in claim 8, the speaker being carried by a plate, the membrane means being sealed to the plate.

10. A prosthesis as claimed in claim 9, the plate being hollow, the speaker being within the plate, and a hole through the plate into a volume between the membrane means and the plate.

* * * * *